(12) United States Patent
Preiss et al.

(10) Patent No.: US 6,649,717 B1
(45) Date of Patent: Nov. 18, 2003

(54) STABILIZED COMPOSITION OF O- AND N-VINYL COMPOUNDS AND USE OF AMMONIUM SALTS AS STABILIZERS

(75) Inventors: Thomas Preiss, Ludwigshafen (DE); Rudolf Erich Lorenz, Ludwigshafen (DE); Sabine Weiguny, Freinsheim (DE); Jochem Henkelmann, Mannheim (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 0 days.

(21) Appl. No.: 09/913,535

(22) PCT Filed: Feb. 2, 2000

(86) PCT No.: PCT/EP00/00821
§ 371 (c)(1),
(2), (4) Date: Aug. 15, 2001

(87) PCT Pub. No.: WO00/48974
PCT Pub. Date: Aug. 24, 2000

(30) Foreign Application Priority Data

Feb. 16, 1999 (DE) .......................... 199 06 316

(51) Int. Cl.[7] .................................................. C08F 2/00
(52) U.S. Cl. .................. 526/236; 526/259; 526/264; 526/303.1; 526/307.3; 526/307.5; 526/332; 526/334
(58) Field of Search ................. 526/236, 259, 526/264, 303.1, 307.3, 307.5, 332, 334

(56) References Cited

U.S. PATENT DOCUMENTS

| | | | |
|---|---|---|---|
| 3,248,440 A | 4/1966 | Albert | 260/666 |
| 3,892,698 A | * 7/1975 | Burke, Jr. | 260/29.6 XA |
| 5,691,462 A | 11/1997 | Miller et al. | 568/580 |
| 5,744,566 A | * 4/1998 | Tsutsui et al. | 526/336 |
| 6,147,145 A | 11/2000 | Aumueller et al. | 524/86 |

FOREIGN PATENT DOCUMENTS

| | | |
|---|---|---|
| DE | 1286015 | 1/1969 |
| DE | 19609312 | 9/1997 |
| WO | 97/32833 | 9/1997 |

OTHER PUBLICATIONS

*Ullmann's Enc. of Ind. Chem.*, vol. 27, 5th Ed., pp. 435–441, 1996.

* cited by examiner

Primary Examiner—Helen L. Pezzuto
(74) Attorney, Agent, or Firm—Keil & Wienkauf

(57) ABSTRACT

The invention encompasses a composition of vinyl compounds, comprising
a) at least one polymerizable compound which has at least one O-vinyl group or one N-vinyl group, and
b) at least one ammonium salt of the formula (I)

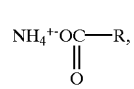

where R is $NH_2$, $O^- NH_4^+$, $C_1$–$C_{18}$-alkyl, $C_6$–$C_{18}$-cycloalkyl, or $C_7$–$C_{18}$-alkylcycloalkyl.

The invention further relates to the use of an ammonium salt of the formula (I) as additive to polymerizable compounds which have at least one O-vinyl group or one N-vinyl group, and also to a process for inhibiting premature polymerization of compositions which comprise polymerizable compounds which have at least one O-vinyl group or one N-vinyl group, which encompasses adding to the compositions an ammonium salt of the formula (I).

13 Claims, No Drawings

STABILIZED COMPOSITION OF O- AND N-VINYL COMPOUNDS AND USE OF AMMONIUM SALTS AS STABILIZERS

The invention relates to stabilized compositions of O- or N-vinyl compounds, to a process for stabilizing O- or N-vinyl compounds, and to the use of the stabilizers.

Vinyl compounds where the vinyl group or the vinyl groups have bonding via oxygen or nitrogen to the main skeleton of the compound, known as O- or N-vinyl compounds, have a tendency toward spontaneous and strongly exothermic cationic polymerization, in particular in the presence of acid. In the case of vinyl ethers, furthermore, creeping polymerization to give polyvinyl ethers is observed, and vinylamines/amides are similarly found to give polyvinylamines/amides. Even storage under inert conditions does not inhibit the polymerization.

O-Vinyl ethers, which are of particular commercial importance, are used as monomers in the production of a wide variety of homo- or copolymerized products, and serve as reactive diluents in surface coatings. In this application sector it is essential to inhibit premature polymerization. When O-vinyl ethers are stored under inert conditions, the presence of polyvinyl ether oligomers can be detected even after a few weeks with the aid of gel permeation chromatography (GPC). The monomer content determined by gas chromatography (GC) decreases correspondingly. The formation of toxic acetaldehyde also indicates the decomposition of the O-vinyl ether. Without addition of a stabilizer, even after a few weeks the acetaldehyde content is sometimes 800 ppm or above. If O-vinyl ethers also contain other functional groups, such as hydroxyl, spontaneous intra- or intermolecular acetalization can occur.

Stabilizers which have been known for a long time are alkali metal hydroxides, specifically KOH (Ullmann's Encyclopedia of Industrial Chemistry, volume 27, 5th edition, pp. 435–441, specifically p. 440, VCH-Verlagsgesellschaft mbH, Weinheim). However, these stabilizers, such as KOH, are not soluble in every vinyl ether, and this means that relatively large amounts of hydroxides have to be added and settle at the base of the vessels. The use of relatively large amounts of hydroxides is problematic, since the hydroxides comprise considerable amounts of water and also sometimes liberate water by deprotonating alcohols. This water brings about the decomposition of vinyl ethers into acetaldehyde and alcohol. Acetaldehyde is slightly toxic and causes odor-impairment of the product. It is also known that the use of KOH brings about discoloration of the product. This reduces the scope of application and reduces the maximum storage time of vinyl ethers.

U.S. Pat. No. 5,691,462 discloses that the alkali metal salts of an unsubstituted $C_1$–$C_{14}$ carboxylic acid can be used as stabilizers for vinyl ethers. Examples mentioned are sodium acetate, potassium acetate, sodium carbonate and potassium carbonate. Although the vinyl ether compositions stabilized with these substances are more colorfast than KOH-stabilized compositions, the suppression of acetaldehyde formation is unsatisfactory.

DE-A-1 286 015 stabilizes aromatic vinyl compounds, such as styrene, with respect to polymerization by adding, as stabilizers, hydroxyammonium acetates of the formula $CH_3COO[NH(OH)R_1R_2]$, where each of $R_1$ and $R_2$ is alkyl having from 1 to 6 carbon atoms.

DE-A 196 09 312 stabilizes monomer compositions with respect to polymerization by adding N-oxyl compounds of a secondary amine which has no hydrogen atoms on the α-carbon atoms, the monomers having certain vinyl groups.

It is an object of the present invention to provide stabilized compositions of vinyl compounds which firstly have good colorfastness and secondly have a low decomposition rate. A further object of the invention is to provide substances which can be used as stabilizing additives to vinyl compounds and which give the resultant compositions the properties mentioned. The additives should be low-cost, have satisfactory solubility, and also be capable of removal from the vinyl compounds.

We have found that this object is achieved by means of a composition of vinyl compounds, comprising a) at least one polymerizable compound which has at least one O-vinyl group or one N-vinyl group, and b) at least one ammonium salt of the formula (I)

where R is $NH_2$, $O^- NH_4^+$, $C_1$–$C_{18}$-alkyl, $C_6$–$C_{18}$-cycloalkyl, or $C_7$–$C_{18}$-alkylcycloalkyl.

Ammonium salts of the formula (I) can be prepared in relatively anhydrous form and are low-cost. Addition of these ammonium salts to the polymerizable compounds of component a) has been found to suppress premature polymerization of these compounds, while the change in color of the resultant composition of the invention is markedly smaller than with addition of the known compounds. It has moreover been found that the inventive ammonium salts of the formula (I) dissolve or disperse relatively readily in the polymerizable compounds of component a), and are nevertheless readily removable. The resultant compositions of the invention are easy to pump.

For the purposes of the present invention, a polymerizable compound which has at least one O-vinyl group or one N-vinyl group is a heterosubstituted vinyl monomer bearing oxygen or nitrogen as heteroatom at the vinyl group. Examples of heterosubstituted vinyl monomers which may be used are vinyl carboxylates, such as vinyl acetate, vinyl propionate or vinyl butyrate, vinyl ethers, such as methyl vinyl ether, ethyl vinyl ether or butyl vinyl ether, triethylene glycol vinyl ether, hydroxyalkyl vinyl ethers, such as hydroxybutyl vinyl ether, and cycloalkyl vinyl ethers, such as cyclohexyl vinyl ether, and also vinylcarbazoles, vinylpyrrolidones, vinylphthalimides, vinylcaprolactams, vinylimidazoles and vinylformamide.

Preferred ammonium salts are ammonium carbonamate, ammonium carbonate and the ammonium salts of methanoic, ethanoic, propanoic, isopropanoic, butanoic, isobutanoic, tert-butanoic, pentanoic, isopentanoic, hexanoic or cyclohexanoic acids, and mixtures of these.

Particularly preferred ammonium salts are ammonium carbonate $((NH_4)_2CO_3)$ and ammonium carbamate $(NH_4NH_2CO_2)$.

In another embodiment of the composition of the invention, at least one polymerizable compound of component a) is covered by the formula (II)

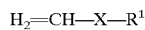

where
X is O or $NR^2$,
$R^1$ is $$\overset{O}{\underset{}{\|}}_{C-R^3}$$

or $R^3$, $R^2$ is hydrogen or $C_1$–$C_4$-alkyl or, together with $R^3$, is a $C_3$, $C_4$, or $C_5$ alkylene bridge or alkenylene bridge, in which up to two non-adjacent $CH_2$ groups may have been replaced by NH, N($C_1$–$C_4$-alkyl), N($C_6$–$C_{10}$-aryl) or oxygen, and up to two non-adjacent CH groups may have been replaced by N, and $R^3$ is hydrogen or a singly or multiply hydroxyl-substituted or vinyloxy-substituted or unsubstituted $C_1$–$C_{16}$-alkyl-, $C_6$–$C_{16}$-cycloalkyl- or $C_1$–$C_4$-alkyl-$C_6$–$C_{12}$-cycloalkyl group or, together with $R^2$, is a $C_3$, $C_4$ or $C_5$ alkylene bridge or alkenylene bridge, in which up to two non-adjacent $CH_2$ groups may have been replaced by NH, N($C_1$–$C_4$-alkyl), N($C_6$–$C_{10}$-aryl) or oxygen, and up to two non-adjacent CH groups may have been replaced by N.

X in the polymerizable compounds of the formula (II) present in the composition of the invention is preferably oxygen. Vinyl ethers where $R^1$ is $C_1$–$C_4$-alkyl, i.e. methyl, ethyl, n-propyl, isopropyl, n-butyl, isobutyl, sec-butyl or tert-butyl, are preferred polymerizable compounds. Preference is also given to vinyl ethers where $R^1$ is $C_1$–$C_4$-hydroxyalkyl or $C_1$–$C_4$-alkyl with one vinyloxy substituent.

Other embodiments of the composition of the invention are those which comprise, as polymerizable compound, triethylene glycol divinyl ether (DVE), 4-hydroxybutyl vinyl ether, and/or cyclohexyl vinyl ether. If X is $NR^2$, $R^1$ is preferably CO—$R^3$.

Radicals $R^3$ which may be used, besides hydrogen and the $C_1$–$C_4$-alkyl groups mentioned, are radicals which together with $NR^2$ form a saturated or unsaturated 5- to 7-membered ring. Examples of ring systems of this type are those of the formula (III)

(III)

In another embodiment of the composition of the invention, X—$R^1$ is $NH_2COCH_3$, N-imidazolyl, N-pyrrolidinonyl or N-caprolactamyl.

The invention further provides the use of an ammonium salt of the formula (I) as additive to polymerizable compounds which have at least one O-vinyl group or one N-vinyl group.

Another embodiment of the invention is the use of ammonium carbonate (($NH_4$)$_2CO_3$) or of ammonium carbamate ($NH_4NH_2CO_2$) as additive to polymerizable compounds which have at least one O-vinyl group or one N-vinyl group.

The invention further provides a process for inhibiting premature polymerization of compositions which comprise polymerizable compounds which have at least one O-vinyl group or one N-vinyl group, which encompasses adding to the compositions an ammonium salt of the formula (I).

In another embodiment of the process of the invention, the ammonium salt used is ammonium carbonate (($NH_4$)$_2CO_3$) or ammonium carbamate ($NH_4NH_2CO_2$).

The examples provide further description of the invention.

EXAMPLE 1

Freshly distilled triethylene glycol divinyl ether (DVE-3) with 98.8% or 99.8% by area (GC) purity and with a color number<5 APHA, and comprising no oligomeric contaminants detectable by gel permeation chromatography (GPC) is stored for a prolonged period under an inert gas, i.e. under inert conditions, in a brown gas bottle at room temperature (23° C.) or at 50° C. The results are seen in Tables 1.1 and 1.2:

TABLE 1.1

DVE-3 unstabilized at 50° C.

|  | DVE-3 area % | APHA | AA |
| --- | --- | --- | --- |
| Directly after addition | 98.8 | 4 | <5 |
| Week 2 | 98.5 | 2 | 44 |
| Week 4 | 98.6 | 0 | 110 |
| Week 6 | 98.7 | 9 | 160 |
| Week 8 | 98.5 | 6 | 160 |
| Week 10 | 98.9 | 5 | 200 |

Polymeric constituents (GPC): 11 554 (After 8 weeks)

TABLE 1.2

DVE-3 unstabilized at room temperature

|  | DVE-3 area % | APHA | AA |
| --- | --- | --- | --- |
| Directly after addition | 98.81 | <5 | <5 |
| Week 4 | 99.76 | 7 | 6 |
| Week 6 | 99.77 | 14 | 12 |
| Week 12 | 99.75 | 7 | 25 |
| Week 16 | 99.73 | 7 | 31 |
| Week 20 | 99.74 | 6 | 40 |
| Week 24 | 99.74 | 5 | n.d. |
| Week 28 | 99.65 | 11 | 45 |

Polymeric constituents (GPC): 50 (after 16 weeks at room temperature)

n.d. not determined

AA: AA is the acetaldehyde content in ppm, determined by headspace-capillary GC apparatus with flame ionization detection (FID). A fused silica capillary provided with 100% polydimethylsiloxane was used for the separation. Results were quantified by the standard addition method.

GC column: Fused silica capillary provided with 100% polydimethylsiloxane as stationary phase, e.g. DB 1 from the company J & W Scientific, length 30 m, internal diameter 0.25 mm, film thickness 1 μm.

Specimen weight: The specimen weight was matched to the proportions by weight to be determined.

Calibration: Calibration was carried out by adding defined amounts of suitably concentrated standard solutions of acetaldehyde dissolved in dimethylacetamide to separately weighed portions of specimens.

Analysis parameters: Temperature-control conditions for the Headspace-GC apparatus: 40° C., transfer line temperature: 120° C., specimen injection: injection time 6 seconds, oven heating program: 5 min. isothermal at 50° C., from 50° C. to 230° C. at 5 K/min., 10 min. isothermal at 230° C., detector temperature (FID):

250° C., carrier gas: helium (inlet pressure 0.7 bar), split about 10 ml/min.

APHA: APHA is a color number of the American Public Health Association, as in Römpp, Chemielexikon, Georg Thieme Verlag Stuttgart, 1995.

Area%: is the proportion of the respective ether determined by gas chromatography (GC) and given in "% by area". Use was made here of a DB-Wax column with 0.25 μm internal diameter. Measurement program: initial temperature 50° C. isothermal for 5 min., from 50 to 240° C. at 10 K/min., detector temperature (FID) 250° C.

Polymeric Constituents (GPC):

The polymeric constituents were calculated using gel permeation chromatography. The polymeric constituents (GPC) data are $$= \frac{area_{sp.}}{C_{sp.}},$$

indicating the amount of polymeric constituents measured in mV·s·ml/mg. $area_{sp.}$ is the area [mV·s] found for the specimen peak eluting at the cut-off (high molecular weight fraction). $C_{sp.}$ is the weight of the specimen in 1 ml of eluent [mg/ml].

The value was recorded once the listed number of weeks had passed after addition to the ether of the stabilizer to be tested. Unless otherwise stated, specimens analyzed by GPC were stored at 50° C.

T: Temperature of the storage tests. To determine the various measurements, appropriate aliquots were removed from the test specimen after appropriate periods, and the specimen was then stored again under inert gas.

Table 1.3 shows the results from storage of DVE-3 with addition of 0.01% (by weight) of potassium carbonate at 50 and, respectively, 70° C.

TABLE 1.3

|  | 50° C. | | | 70° C. | | |
|---|---|---|---|---|---|---|
| DVE-3 with 0.01% $K_2CO_3$ | DVE-3 area % | APHA | AA | DVE-3 area % | APHA | AA |
| Directly after addition | 98.9 | 2 | 39 | 98.9 | 3 | 40 |
| Week 2 | 98.7 | 2 | 71 | 98.7 | 5 | 59 |
| Week 4 | 98.78 | 7 | 110 | 98.8 | 26 | 110 |
| Week 6 | 98.8 | 20 | 140 | 98.7 | 122 | 130 |
| Week 8 | 98.0 | 35 | 76 | 99 | 219 | 79 |

Polymeric constituents (GPC): 1256 (after 8 weeks)

Table 1.4 shows the results from storage of DVE-3 with addition, according to the invention, of 0.01% (by weight) of ammonium carbonate at 50 and, respectively, 70° C.

TABLE 1.4

|  | 50° C. | | | 70° C. | | |
|---|---|---|---|---|---|---|
| DVE-3 with 0.01% $(NH_4)_2CO_3$ | DVE-3 area % | APHA | AA | DVE-3 area % | APHA | AA |
| Directly after addition | 98.8 | n.d. | n.d. | 98.8 | n.d. | n.d. |
| Week 2 | 98.8 | 37 | 21 | 98.8 | 225 | 16 |
| Week 4 | 98.98 | 16 | 37 | 98.93 | 300 | 29 |
| Week 6 | 98.9 | 63 | 62 | 98.85 | 286 | 45 |
| Week 8 | 98.6 | 71 | 91 | 98.7 | 360 | 46 |

Polymeric constituents (GPC): 3650 (after 4 weeks)

Table 1.5 shows the results with 0.01% (by weight) of potassium hydroxide.

TABLE 1.5

|  | 50° C. | | | 70° C. | | |
|---|---|---|---|---|---|---|
| DVE-3 with 0.01% KOH | DVE-3 area % | APHA | AA | DVE-3 area % | APHA | AA |
| Directly after addition | 98.9 | 2 | 40 | 98.9 | 3 | 40 |
| Week 2 | 98.7 | 265 | 24 | 98.7 | 186 | 46 |
| Week 4 | 98.56 | 175 | 61 | 98.8 | 205 | 100 |
| Week 6 | 98.9 | 166 | 91 | 98.9 | 418 | 140 |
| Week 8 | 98.9 | 131 | 72 | 98.9 | 597 | 100 |

Polymeric constituents (GPC): 6873 (after 4 weeks)

Table 1.6 shows the results with 0.01% (by weight) of sodium hydroxide.

TABLE 1.6

|  | 50° C. | | | 70° C. | | |
|---|---|---|---|---|---|---|
| DVE-3 with 0.01% NaOH | DVE-3 area % | APHA | AA | DVE-3 area % | APHA | AA |
| Directly after addition | 99.58 | 5 | 18 | 99.58 | 5 | 18 |
| Week 2 | 99.52 | 3 | 110 | 99.58 | 16 | 63 |
| Week 4 | 99.33 | 13 | 170 | 99.29 | 69 | 94 |

It can be seen that the stabilizer substance ammonium carbonate of the invention effectively suppresses the premature polymerization of triethylene glycol divinyl ether, and the color shift here is substantially smaller than when using potassium hydroxide. In addition, ammonium carbonate effectively slows the decomposition of triethylene glycol divinyl ether, which is revealed by formation of acetaldehyde.

EXAMPLE 2

The procedure in Example 2 is as in Example 1, but 4-hydroxybutyl vinyl ether (HBVE) replaces triethylene glycol divinyl ether. The information given on test procedures is similarly applicable here.

Table 2.1 shows the results by addition of 0.01% (by weight) of potassium carbonate at 50 and, respectively, 70° C.

TABLE 2.1

| HBVE | 50° C. | | | 70° C. | | |
|---|---|---|---|---|---|---|
| with 0.01% $K_2CO_3$ | HBVE area % | APHA | AA | HBVE area % | APHA | AA |
| Directly after addition | 98.85 | n.d. | n.d. | 99.06 | n.d. | n.d. |
| Week 2 | 98.62 | 11 | 130 | 98.52 | 18 | 270 |
| Week 4 | 98.60 | 16 | 250 | 98.70 | 45 | 52 |
| Week 6 | 98.87 | 13 | 340 | 98.00 | 16 | 580 |
| Week 8 | 98.70 | 11 |  | 97.00 | 9 |  |

Polymeric constituents (GPC): 104 (after 6 weeks)

Table 2.2 shows the results from the inventive addition of 0.01% (by weight) of ammonium carbonate.

TABLE 2.2

| HBVE with 0.01% $(NH_4)_2CO_3$ | 50° C. | | | 70° C. | | |
|---|---|---|---|---|---|---|
| | HBVE area % | APHA | AA | HBVE area % | APHA | AA |
| Directly after addition | 98.20 | n.d. | n.d. | 98.80 | n.d. | n.d. |
| Week 2 | 98.00 | 14 | 22 | 97.70 | 22 | 23 |
| Week 4 | 97.52 | 22 | 24 | 97.24 | 43 | 28 |
| Week 6 | 98.06 | 28 | 34 | 96.30 | 46 | 35 |
| Week 8 | 97.20 | 38 | 46 | 95.70 | 67 | 53 |

Polymeric constituents (GPC): 52 (after 6 weeks)

Table 2.3 shows the results on adding 0.01% (by weight) of ammonium carbamate.

TABLE 2.3

| HBVE with 0.01% ammonium carbamate | 50° C. | | | 70° C. | | |
|---|---|---|---|---|---|---|
| | HBVE area % | APHA | AA | HBVE area % | APHA | AA |
| Directly after addition | 96.20 | n.d. | n.d. | 95.9 | n.d. | n.d. |
| Week 2 | 96.10 | 17 | 41 | 94.9 | 55 | 39 |
| Week 4 | 95.94 | 27 | 48 | 94.05 | 115 | 45 |
| Week 6 | 96.40 | 35 | 61 | 92.5 | 141 | 71 |
| Week 8 | 96.00 | 59 | 75 | 91.8 | 211 | 80 |

Polymeric constituents (GPC): 51 (after 6 weeks)

It can be seen that the stabilizer substances ammonium carbonate and ammonium carbamate of the invention are substantially better than the known stabilizer substance potassium carbonate at suppressing the premature polymerization of 4-hydroxybutyl vinyl ether. In addition, although the color shift given by the stabilizers of the invention is somewhat greater than with potassium carbonate, they are substantially more effective than the known potassium carbonate in suppressing the formation of decomposition products, such as acetaldehyde. Potassium hydroxide proved to be completely unusable in this test, and comparison was therefore dispensed with.

EXAMPLE 3

Cyclohexyl vinyl ether (CHVE) was used in this example. The procedure was otherwise as in Examples 1 and 2.

Table 3.1 lists the results for cyclohexyl vinyl ether without stabilizer and at room temperature.

TABLE 3.1

| CHVE unstabilized at room temperature | | | |
|---|---|---|---|
| | CHVE-3 area % | APHA | AA |
| Directly after addition | 99.85 | <5 | 120 |
| Week 4 | 99.79 | 5 | 310 |
| Week 8 | 99.78 | 3 | 350 |
| Week 12 | 99.78 | 8 | 590 |
| Week 16 | 99.77 | <5 | 770 |
| Week 20 | 99.74 | 3 | 640 |
| Week 24 | 99.73 | <5 | n.d. |
| Week 28 | 99.57 | 5 | 510 |

Polymeric constituents (GPC): 881 (after 16 weeks at room temperature)

Table 3.2 shows the results on adding 0.1% (by weight) of potassium carbonate.

TABLE 3.2

| CHVE with 0.1% $K_2CO_3$ | 50° C. | | |
|---|---|---|---|
| | CHVE area % | APHA | AA |
| Directly after addition | 99.82 | 3 | 10 |
| Week 2 | 99.72 | 5 | 180 |
| Week 4 | 99.7 | 11 | 220 |
| Week 6 | 99.64 | 12 | 250 |
| Week 8 | 99.7 | 29 | 170 |
| Week 10 | 99.7 | 33 | 200 |

Polymeric constituents (GPC): 173 (after 6 weeks)

Table 3.3 shows the results on addition, according to the invention, of 0.01% (by weight) of ammonium carbonate.

TABLE 3.3

| CHVE with 0.01% $(NH_4)_2CO_3$ | 50° C. | | | 70° C. | | |
|---|---|---|---|---|---|---|
| | CHVE area % | APHA | AA | CHVE area % | APHA | AA |
| Directly after addition | 99.8 | <5 | 16 | 99.8 | <5 | 16 |
| Week 2 | 99.7 | 3 | 12 | 99.8 | 8 | 17 |
| Week 4 | 99.7 | 10 | 23 | 99.74 | 25 | 26 |
| Week 6 | 99.66 | 14 | 19 | 99.7 | 33 | 20 |
| Week 8 | 99.5 | 29 | 56 | 99.5 | | n.d. |

Polymeric constituents (GPC): 60 (after 6 weeks)

Table 3.4 shows the results with 0.01% (by weight) of ammonium carbamate.

TABLE 3.4

| CHVE with 0.01% Ammonium carbamate | 50° C. | | | 70° C. | | |
|---|---|---|---|---|---|---|
| | CHVE area % | APHA | AA | CHVE area % | APHA | AA |
| Directly after addition | 99.8 | <5 | 16 | 99.8 | <5 | 16 |
| Week 2 | 99.74 | 6 | 20 | 99.76 | 19 | 10 |
| Week 4 | 98.73 | 13 | 40 | 99.71 | 41 | 22 |
| Week 6 | 98.73 | 13 | 45 | 99.55 | 91 | 20 |
| Week 8 | 99.73 | 22 | 56 | 97.7 | n.d. | n.d. |

Polymeric constituents (GPC): 125 (after 6 weeks)

Table 3.5 lists the results on adding 0.01% (by weight) of potassium hydroxide.

TABLE 3.5

| CHVE with 0.1% KOH | 50° C. | | |
|---|---|---|---|
| | CHVE area % | APHA | AA |
| Directly after addition | 99.82 | 3 | 10 |
| Week 2 | 99.72 | 5 | 170 |
| Week 4 | 99.7 | 11 | 190 |
| Week 6 | 99.65 | 24 | 230 |
| Week 8 | 99.7 | 46 | 130 |
| Week 10 | 99.7 | 44 | 170 |

Polymeric constituents (GPC): 151 (after 6 weeks)

The stabilizer substances ammonium carbonate and ammonium carbamate of the invention suppress the polymerization of cyclohexyl vinyl ether substantially more effectively than do the stabilizer substances of the prior art, potassium carbonate and potassium hydroxide. Although the color shift given by the stabilizer substances of the invention is approximately comparable to that given by the stabilizer substances potassium hydroxide and potassium carbonate, the stabilizer substances of the invention are substantially more effective in inhibiting the decomposition of cyclohexyl vinyl ether to give acetaldehyde.

We claim:

1. A composition of vinyl compounds, comprising
   a) at least one polymerizable compound which has at least one O-vinyl group or one N-vinyl group, and
   b) at least one ammonium salt of the formula (I)

$$NH_4^{+-}OC\underset{\underset{O}{\|}}{-}R, \qquad (I)$$

where R is $NH_2$, $-O^- NH_4^+$, $C_1-C_{18}$-alkyl, $C_6-C_{18}$-cycloalkyl, or $C_7-C_{18}$-alkylcycloalkyl.

2. A composition as claimed in claim 1, wherein the ammonium salt of component b) is $(NH_4)_2CO_3$ or $NH_4NH_2CO_2$.

3. A composition as claimed in claim 1, wherein at least one polymerizable compound of component a) is covered by the formula (II)

$$CH_2=CH-X-R^1 \qquad (II),$$

where

X is O or $NR^2$, $R^1$ is $$\underset{\underset{C-R^3}{\|}}{O}$$

or $R^3$, $R^2$ is hydrogen or $C_1-C_4$-alkyl or, together with $R^3$, is a $C_3$, $C_4$, or $C_5$ alkylene bridge or alkenylene bridge, in which up to two non-adjacent $CH_2$ groups may have been replaced by NH, $N(C_1-C_4$-alkyl), $N(C_6-C_{10}$-aryl) or oxygen, and up to two non-adjacent CH groups may have been replaced by N, and $R^3$ is hydrogen or a singly or multiply hydroxyl-substituted or vinyloxy-substituted or unsubstituted $C_1-C_{16}$-alkyl-, $C_6-C_{16}$-cycloalkyl- or $C_1-C_4$-alkyl-$C_6-C_{12}$-cycloalkyl group or, together with $R^2$, is a $C_3$, $C_4$ or $C_5$ alkylene bridge or alkenylene bridge, in which up to two non-adjacent $CH_2$ groups may have been replaced by NH, $N(C_1-C_4$-alkyl), $N(C_6-C_{10}$-aryl) or oxygen, and up to two non-adjacent CH groups may have been replaced by N.

4. A composition as claimed in claim 1, wherein at least one polymerizable compound of component a) is covered by the formula (II)

$$H_2=CH-X-R^1 \qquad (II),$$

where

X is O or $NR^2$, $R^1$ is $$\underset{\underset{C-R}{\|}}{O}$$

or $R^3$, $R^2$ is hydrogen or $C_1-C_4$-alkyl or, together with $R^3$, is a $C_3$, $C_4$, or $C_5$ alkylene bridge or alkenylene bridge, in which up to two non-adjacent $CH_2$ groups may have been replaced by NH, $N(C_1-C_4$-alkyl), $N(C_6-C_{10}$-aryl) or oxygen, and up to two non-adjacent CH groups may have been replaced by N, and $R^3$ is hydrogen or a singly or multiply hydroxyl-substituted or vinyloxy-substituted or unsubstituted $C_1-C_{16}$-alkyl-, $C_6-C_{16}$-cycloalkyl- or $C_1-C_4$-alkyl-$C_6-C_{12}$-cycloalkyl group or, together with $R^2$, is a $C_3$, $C_4$ or $C_5$ alkylene bridge or alkenylene bridge, in which up to two non-adjacent $CH_2$ groups may have been replaced by NH, $N(C_1-C_4$-alkyl), $N(C_6-C_{10}$-aryl) or oxygen, and up to two non-adjacent CH groups may have been replaced by N and wherein the ammonium salt of component b) is $(NH_4)_2CO_3$ or $NH_4NH_2CO_2$.

5. A composition as claimed in claim 3, wherein X is oxygen.

6. A composition as claimed in claim 5, wherein the polymerizable compound of component a) is triethylene glycol divinyl ether (DVE), 4-hydroxybutyl vinyl ether (HBVE) or cyclohexyl vinyl ether or a mixture of these.

7. A composition as claimed in claim 3, wherein X—$R^1$ is $NH_2COCH_3$, N-imidazolyl, N-pyrrolidinonyl or N-caprolactamyl.

8. Polymerizable compound having at least one O-vinyl group or one N-vinyl group and containing an ammonium salt of the formula (I) as claimed in claim 1 as additive.

9. Polymerizable compound as claimed in claim 8, wherein the ammonium salt is $(NH_4)_2CO_3$ or $NH_4NH_2CO_2$.

10. A process for inhibiting premature polymerization of compositions which comprise polymerizable compounds which have at least one O-vinyl group or one N-vinyl group, which comprises adding to the compositions an ammonium salt of the formula (I) as claimed in claim 1.

11. A process as claimed in claim 10, in which the ammonium salt used is $(NH_4)_2CO_3$ or $NH_4NH_2CO_2$.

12. A stabilized composition of vinyl compounds, comprising at least one polymerizable compound which has at least one O-vinyl group or one N-vinyl group, and at least one compound stabilizing the composition wherein at least one compound stabilizing the composition is at least one ammonium salt of the formula (I)

$$NH_4^{+-}OC\underset{\underset{O}{\|}}{-}R, \qquad (I)$$

where R is $NH_2$, $-O^- NH_4^+$, $C_1-C_{18}$-alkyl, $C_6-C_{18}$-cycloalkyl, or $C_7-C_{18}$-alkylcycloalkyl.

13. Polymerizable compound having at least one O-vinyl group or one N-vinyl group and containing an ammonium salt of the formula (I)

$$NH_4^{+-}OC\underset{\underset{O}{\|}}{-}R, \qquad (I)$$

as additive stabilizing the polymerizable compound, where R is $NH_2$, $-O^- NH_4^+$, $C_1-C_{18}$-alkyl, $C_6-C_{18}$-cycloalkyl, or $C_7-C_{18}$-alkylcycloalkyl.

* * * * *

UNITED STATES PATENT AND TRADEMARK OFFICE
CERTIFICATE OF CORRECTION

PATENT NO.    : 6,649,717 B1
DATED         : November 18, 2003
INVENTOR(S)   : Preiss et al.

It is certified that error appears in the above-identified patent and that said Letters Patent is hereby corrected as shown below:

<u>Column 9,</u>
Line 58, "$H_2=CH-X-R^1$" should be -- $CH_2=CH-X-R^1$ --.
Line 64, "R" in the formula should be -- $R^3$ --.

Signed and Sealed this

Thirtieth Day of December, 2003

JAMES E. ROGAN
*Director of the United States Patent and Trademark Office*